US009095473B2

(12) United States Patent
Gerstle et al.

(10) Patent No.: US 9,095,473 B2
(45) Date of Patent: Aug. 4, 2015

(54) PROCESS FOR MANUFACTURING A PACKAGE OF FOLDED ABSORBENT ARTICLES, AND PACKAGE MADE THEREBY

(75) Inventors: Matthew Gerstle, Appleton, WI (US);
Russell P. George, Appleton, WI (US);
David J. Krysiak, Menasha, WI (US);
Katie A. Boland, Neenah, WI (US);
Adrienne R. Loyd, Neenah, WI (US);
Ruth A. McVettie, Freedom, WI (US);
Steven J. Shimon, Hilbert, WI (US);
Brian L. Alberts, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 977 days.

(21) Appl. No.: 13/227,104

(22) Filed: Sep. 7, 2011

(65) Prior Publication Data

US 2013/0060222 A1    Mar. 7, 2013

(51) Int. Cl.
*A61F 13/15* (2006.01)
*A61F 13/551* (2006.01)

(52) U.S. Cl.
CPC ..... *A61F 13/15747* (2013.01); *A61F 13/55115* (2013.01)

(58) Field of Classification Search
CPC .. A47G 11/00; A47K 2010/428; A61L 15/18; A61L 15/60; B65D 83/00; B65D 85/00
USPC .............. 604/367, 385.101, 385.201, 385.02, 604/379, 380; 206/494
See application file for complete search history.

(56) References Cited

U.S. PATENT DOCUMENTS

| | | | |
|---|---|---|---|
| 4,443,512 A | 4/1984 | Delvaux | |
| 4,655,759 A | 4/1987 | Romans Hess et al. | |
| 5,919,181 A | 7/1999 | Visscher et al. | |
| 6,318,555 B1 | 11/2001 | Kuske et al. | |
| 6,491,165 B2 | 12/2002 | Kuske et al. | |
| 6,673,418 B1 | 1/2004 | Deolivera et al. | |
| 6,702,798 B2 | 3/2004 | Christoffel et al. | |
| 7,021,466 B2 | 4/2006 | Kuske et al. | |
| 7,695,462 B2 | 4/2010 | Sato et al. | |
| 2003/0036739 A1 | 2/2003 | Christoffel et al. | |
| 2004/0078017 A1 | 4/2004 | Koyama et al. | |
| 2004/0134822 A1 | 7/2004 | Otsubo | |

(Continued)

FOREIGN PATENT DOCUMENTS

| | | |
|---|---|---|
| EP | 2 092 918 A1 | 8/2009 |
| GB | 1 336 585 A | 11/1973 |
| JP | 09-099903 A | 4/1997 |
| JP | 2001-019070 A | 1/2001 |

(Continued)

*Primary Examiner* — Melanie Hand
(74) *Attorney, Agent, or Firm* — Kimberly-Clark Worldwide, Inc.

(57) ABSTRACT

A process for manufacturing a package of folded absorbent articles is disclosed. In one embodiment, the process includes providing a plurality of absorbent cores, and embossing at least one fold line into each core, each fold line defining a fold region. The process further includes folding each core along the fold region of each fold line to create a plurality of folded absorbent garments, and placing the plurality of folded absorbent garments into a container. In particular embodiments, each core can include two transversely opposed absorbent ears. The process can include folding each core along the fold region of each fold line to move each ear closer to a longitudinal centerline of the core to create a plurality of folded absorbent garments. A package of folded absorbent articles is also disclosed.

4 Claims, 15 Drawing Sheets

(56) References Cited

U.S. PATENT DOCUMENTS

| | | |
|---|---|---|
| 2004/0211696 A1 | 10/2004 | Underhill et al. |
| 2006/0004343 A1 | 1/2006 | Datta et al. |
| 2008/0312626 A1 | 12/2008 | Koyama et al. |
| 2008/0312627 A1 | 12/2008 | Takeuchi et al. |
| 2011/0066127 A1 | 3/2011 | Kuwano et al. |
| 2011/0192749 A1 | 8/2011 | Hooyman et al. |

FOREIGN PATENT DOCUMENTS

| | | |
|---|---|---|
| JP | 2006-034496 A | 2/2006 |
| JP | 2006-122396 A | 5/2006 |
| JP | 2007-267763 A | 10/2007 |
| KR | 20-0161882 | 9/1997 |
| WO | WO 97/33815 A1 | 9/1997 |
| WO | WO 2004/073570 A1 | 9/2004 |
| WO | WO 2005/110321 A1 | 11/2005 |
| WO | WO 2007/058761 A1 | 5/2007 |

PROCESS FOR MANUFACTURING A PACKAGE OF FOLDED ABSORBENT ARTICLES, AND PACKAGE MADE THEREBY

BACKGROUND

People rely on disposable absorbent articles in their everyday lives, including such garments as adult incontinence products, enuresis pants, training pants, and diapers. A plurality of such articles is typically provided together in a container, such as a flexible bag, for sale to consumers. Frequently, such articles are folded prior to packaging. One example of such folding is disclosed in U.S. Pat. No. 6,702,798 to Christoffel et al., the entirety of which is hereby incorporated by reference to the extent not inconsistent herewith.

Some existing disposable absorbent articles include absorbent cores comprised of fluff and/or superabsorbent polymer. Such cores can create bulk in the article. When the article is folded prior to packaging, this bulk can interfere with the folding process. For example, the bulk of the absorbent core can lead to inconsistent fold locations. When successively manufactured products are not folded in a consistent manner, the resulting package may in certain cases exhibit undesirable bulges or ripples, or may have inadequately "squared" corners. Furthermore, a lack of predictability in the location of folds in the absorbent cores may negatively impact the performance of the product by creating creases or cracks at inopportune locations within the absorbent core of the product. Finally, a lack of consistency in folding can lead to undesirable waste or delay in the manufacturing process, such as when poorly folded articles cause jams in the machinery.

Consequently, what is needed is an improved method of manufacturing folded disposable absorbent articles that has the potential to provide more consistent processability, that has the potential to create more consistent final packages in terms of smoothness and squareness, and that has the potential to minimize negative impact on product performance.

SUMMARY OF THE INVENTION

In one aspect, the present invention relates to a process for manufacturing a package of folded absorbent articles, such as garments. In one embodiment, the process includes providing a plurality of absorbent cores. The process further includes embossing at least one fold line into each core, each fold line defining a fold region. The process further includes folding each core along the fold region of each fold line to create a plurality of folded absorbent garments. The process further includes placing the plurality of folded absorbent garments into a container. In particular embodiments, the process includes embossing at least two fold lines, and more particularly at least four fold lines, into each core. In particular embodiments, each fold line is straight; in other embodiments, each fold line is curved. In particular embodiments, each fold line is continuous and unbroken; in other embodiments, each fold line is discontinuous.

In particular embodiments, the absorbent cores are manufactured in a longitudinal machine direction, and each core defines two longitudinally opposed end edges and two side edges that extend between and interconnect the two end edges. Each absorbent core defines a longitudinal centerline positioned midway between the two side edges, and the fold region of each fold line is substantially parallel to the longitudinal centerline. In particular embodiments, each fold line intersects an end edge and a side edge.

In another embodiment, the process for manufacturing the package of folded absorbent garments includes manufacturing a plurality of absorbent cores, each core defining a longitudinal direction and a transverse direction, each core defining two longitudinally opposed end edges and two side edges that extend between and interconnect the two end edges, each absorbent core defining a longitudinal centerline positioned midway between the two side edges. Each core comprises two transversely opposed absorbent ears, each ear defining a first transverse position. The process further includes embossing two fold lines into each core, each fold line defining a fold region. The process further includes folding each core along the fold region of each fold line to create a plurality of folded absorbent garments, such that each ear assumes a second transverse position, the second transverse position of each ear being closer to the longitudinal centerline than the first transverse position of such ear. The process further includes placing the plurality of folded absorbent garments into a container.

In particular embodiments, the fold region of each fold line extends in the longitudinal direction proximate an ear. In particular embodiments, each fold line defines a non-fold region that extends from the fold region toward the longitudinal centerline. In particular embodiments, each fold region extends along the entirety of each fold line.

In another embodiment, the process includes manufacturing a plurality of absorbent cores, each core defining a longitudinal direction and a transverse direction, each core defining two longitudinally opposed end edges and two side edges that extend between and interconnect the two end edges, each absorbent core defining a longitudinal centerline positioned midway between the two side edges. Each core has two transversely opposed absorbent ears, each ear defining a first transverse position. The process further includes embossing two fold lines into each core, each fold line defining a fold region. The process further includes sandwiching each core between a topsheet layer and a backsheet layer to define a plurality of absorbent assemblies, each absorbent assembly having a front end and a back end. The process further includes providing a front panel web that defines a front panel web waist edge and a front panel web leg edge, and providing a back panel web that defines a back panel web waist edge and a back panel web leg edge, the back panel web being spaced apart from the front panel web. The process further includes attaching the front end of each absorbent assembly to the front panel web and attaching the back end of each absorbent assembly to the back panel web. The process further includes folding each absorbent assembly along a crotch fold line to define a crotch fold and so as to bring the front panel web waist edge into close proximity with the back panel web waist edge. The process further includes cutting both the front panel web and the back panel web at a series of cuts spaced apart in a direction of web travel to define a series of discrete absorbent garments, each article having a front panel, a back panel, and an absorbent assembly. The process further includes connecting each front panel to each back panel along a pair of side seams to define a series of pant-like garments, each article defining a waist opening. The process further includes folding the core of each pant-like garment along the fold region of each fold line to create a plurality of folded absorbent garments, such that each ear assumes a second transverse position, the second transverse position of each ear being closer to the longitudinal centerline than the first transverse position of such ear. The process further includes placing the plurality of folded absorbent garments into a container. In particular embodiments, the process further includes folding each pant-like garment so as to move the crotch fold into closer proximity with the waist opening. In particular embodiments, each fold line is straight, each fold line intersects an end edge and a side edge, and each fold region extends along the entirety of each fold line.

In another aspect, the present invention relates to a package of folded absorbent garments. In particular embodiments, the package comprises a plurality of absorbent garments, each absorbent article comprising an absorbent core. Each core defines a longitudinal direction and a transverse direction perpendicular to the longitudinal direction, two longitudinally opposed end edges, first and second side edges that extend between and interconnect the two end edges, and a longitudinal centerline positioned midway between the first and second side edges. Each core comprises a first absorbent ear defining a first ear side edge and a second absorbent ear defining a second ear side edge. Each core comprises a first embossed fold line proximate the first absorbent ear and a second embossed fold line proximate the second absorbent ear, each embossed fold line defining a fold region. Each core is folded along the fold region of each embossed fold line such that the first ear side edge lies closer to the longitudinal centerline than does the fold region of the first embossed fold line and such that the second ear side edge lies closer to the longitudinal centerline than does the fold region of the second embossed fold line.

DETAILED DESCRIPTION OF PARTICULAR EMBODIMENTS

Figure 1:
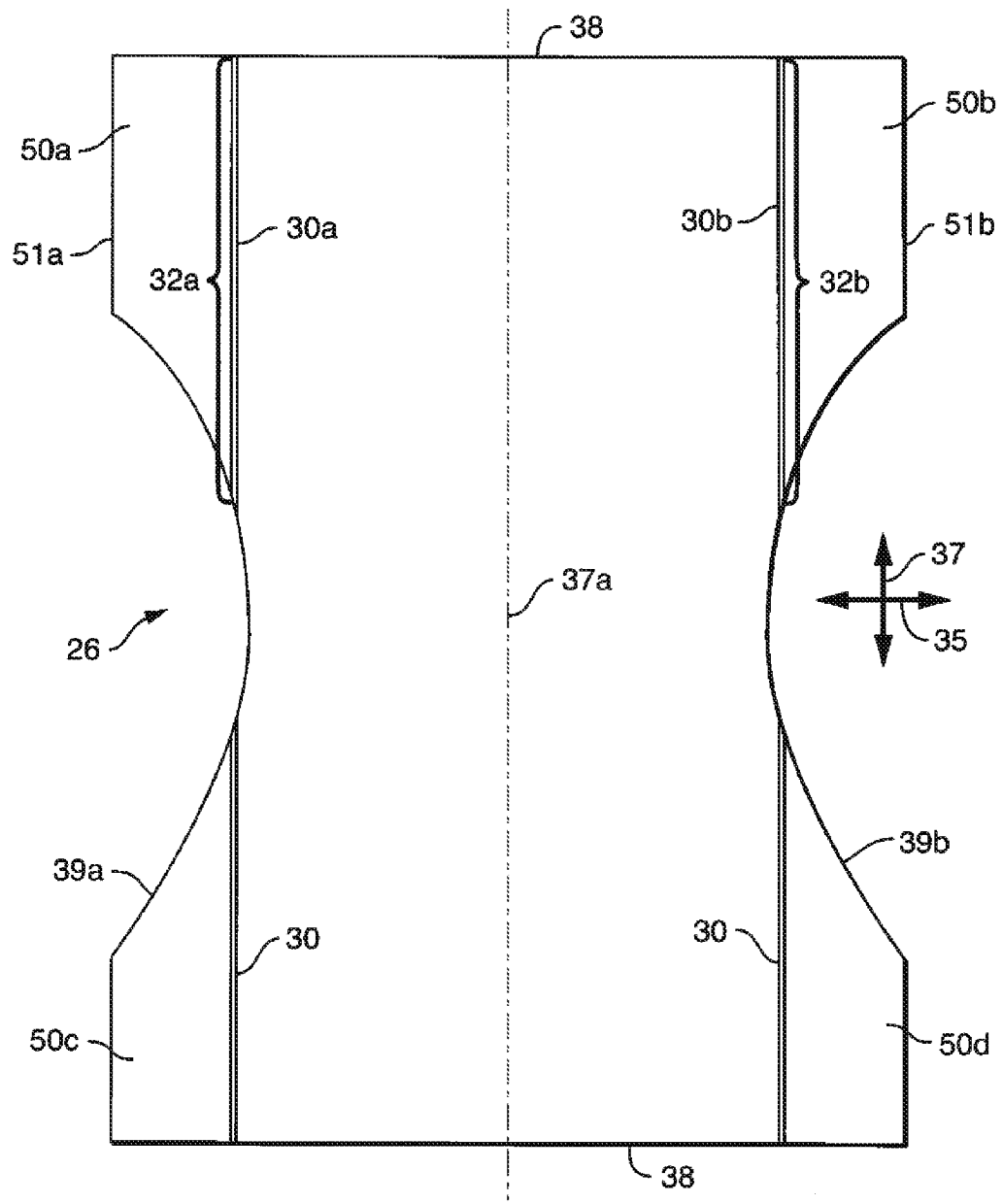
FIG. 1 representatively illustrates a plan view of one embodiment of an absorbent core incorporating principles of the present invention, shown in a laid-flat condition.
Figure 2:
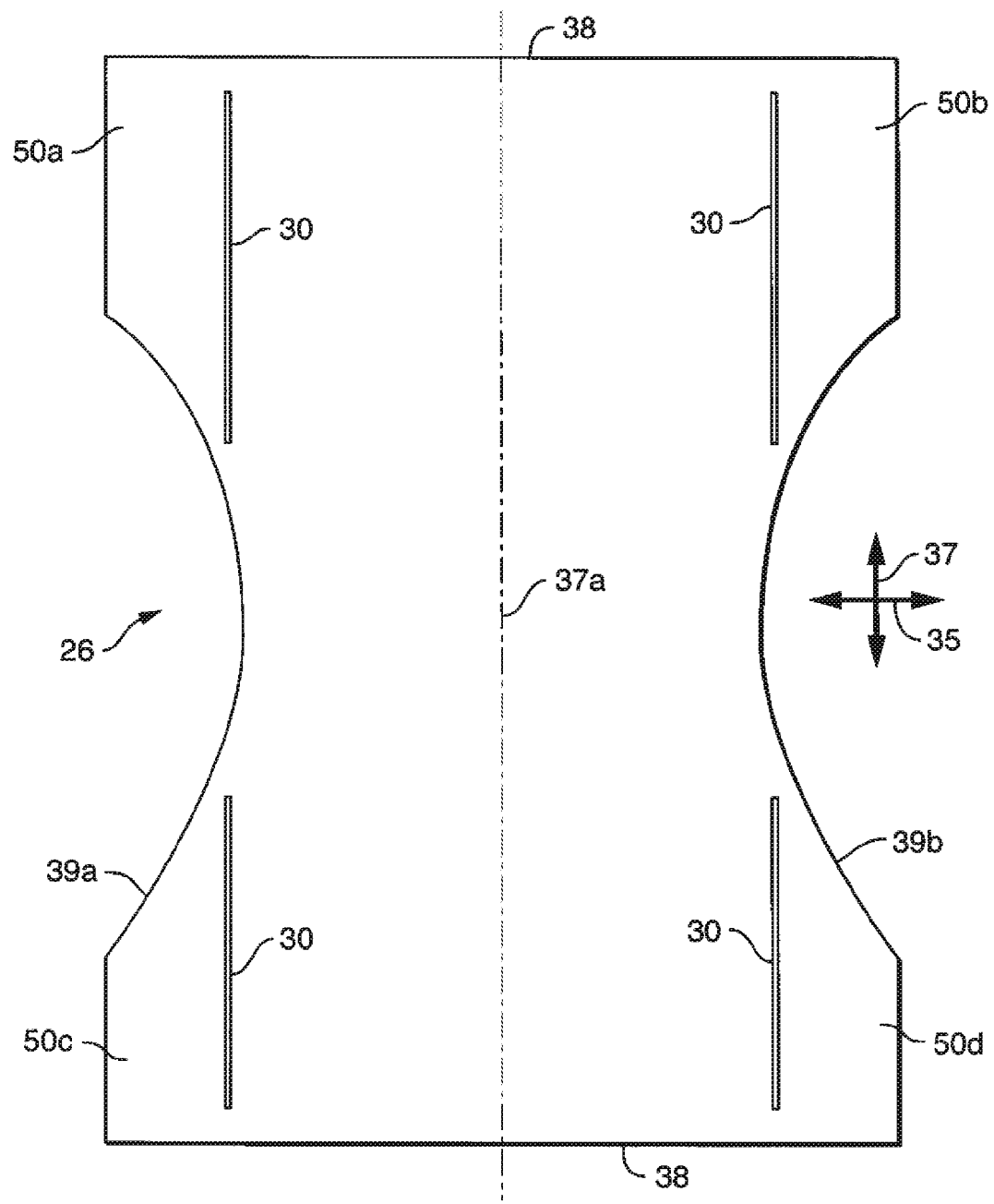
FIG. 2 representatively illustrates a plan view of another embodiment of an absorbent core incorporating principles of the present invention, shown in a laid-flat condition.
Figure 3:
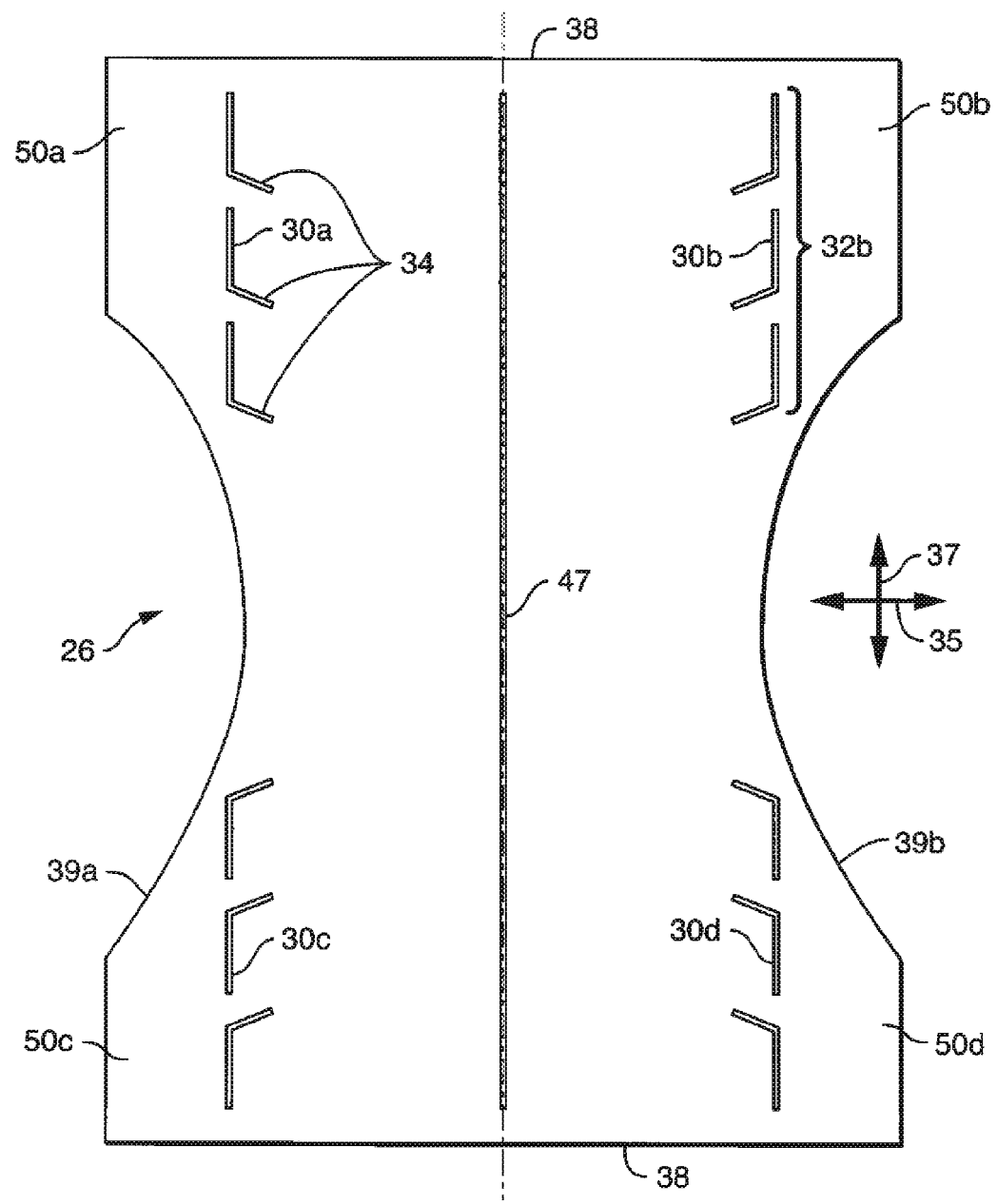
FIG. 3 representatively illustrates a plan view of another embodiment of an absorbent core incorporating principles of the present invention, shown in a laid-flat condition.
Figure 4:
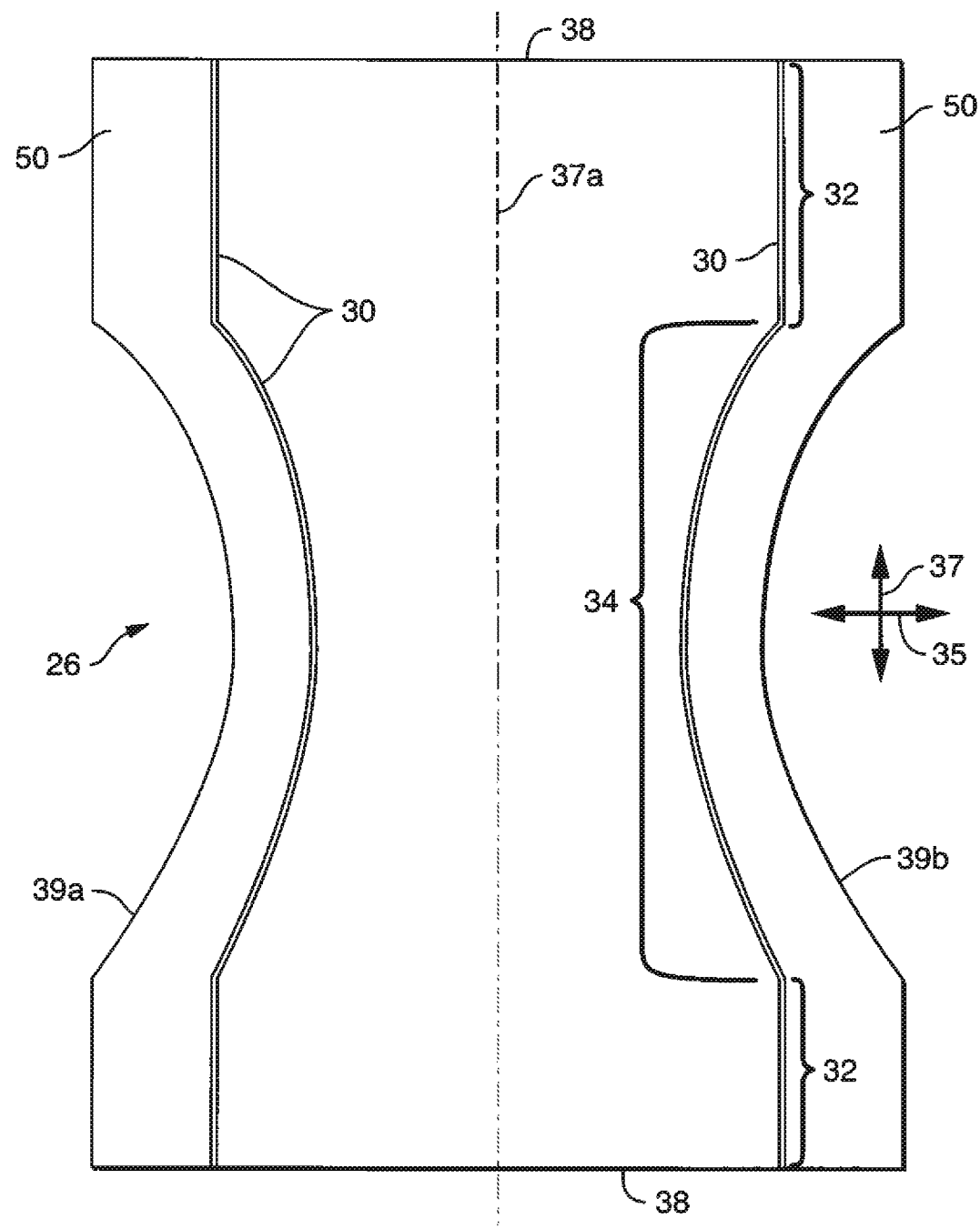
FIG. 4 representatively illustrates a plan view of another embodiment of an absorbent core incorporating principles of the present invention, shown in a laid-flat condition.
Figure 5:
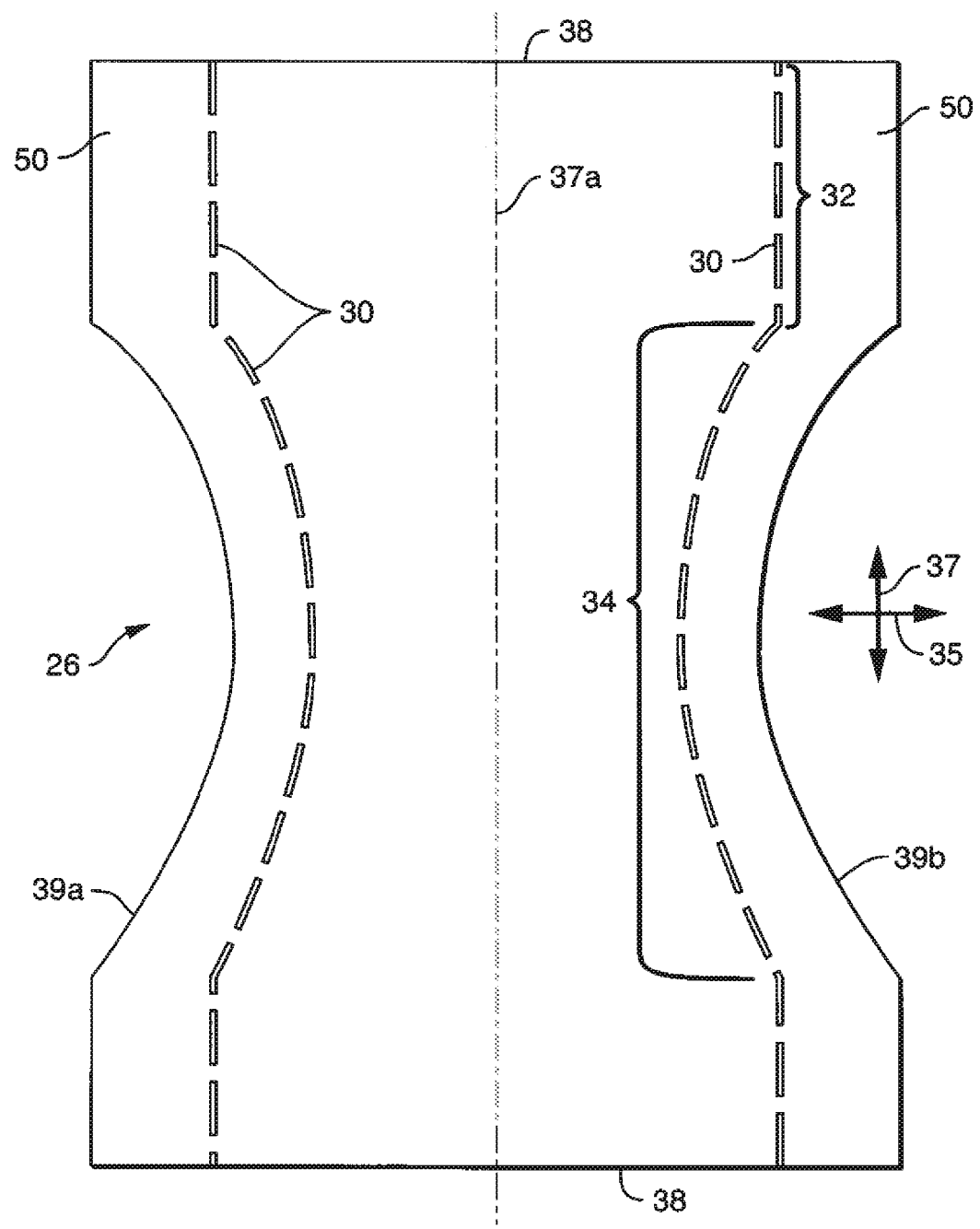
FIG. 5 representatively illustrates a plan view of another embodiment of an absorbent core incorporating principles of the present invention, shown in a laid-flat condition.
Figure 6:
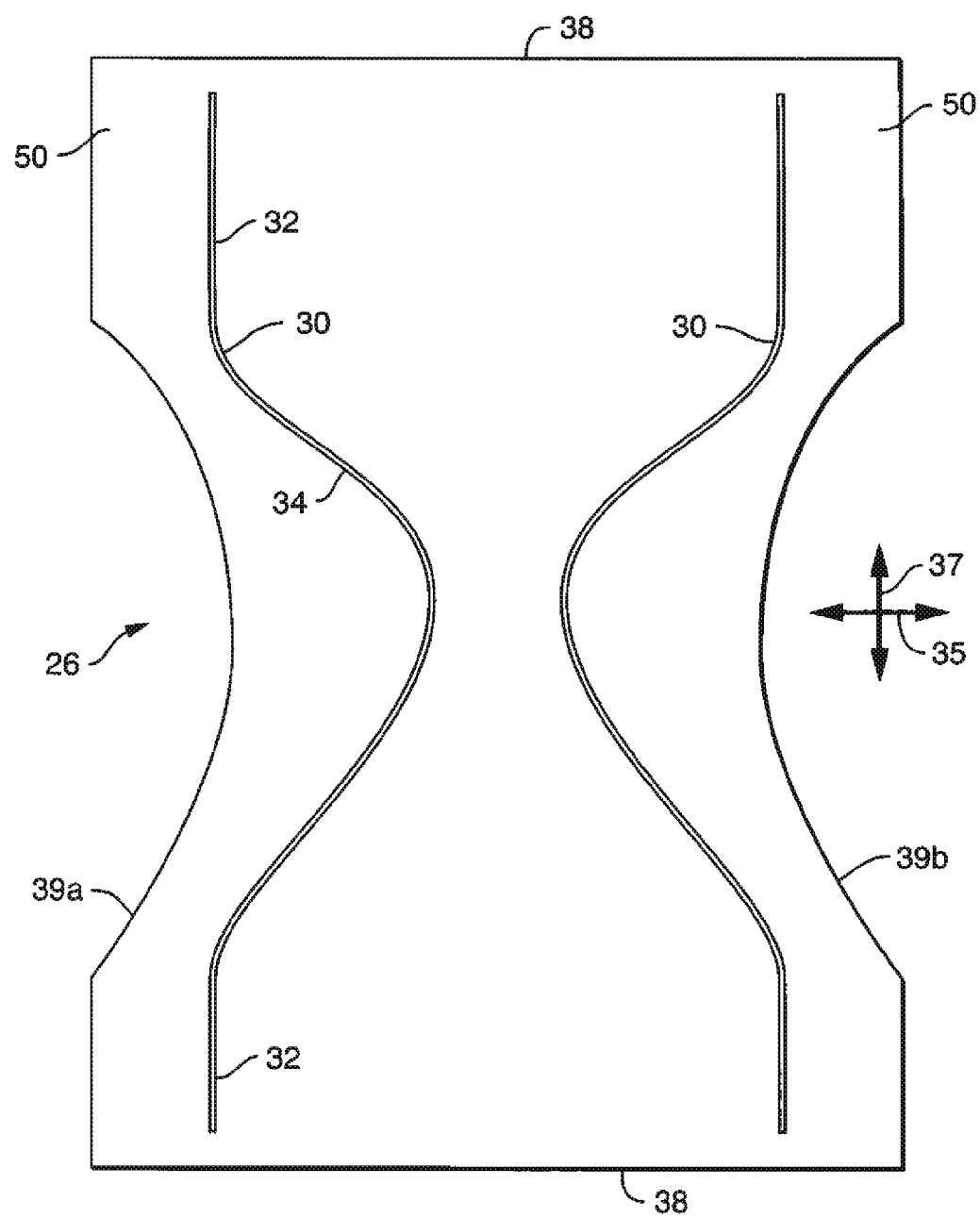
FIG. 6 representatively illustrates a plan view of another embodiment of an absorbent core incorporating principles of the present invention, shown in a laid-flat condition.
Figure 7:
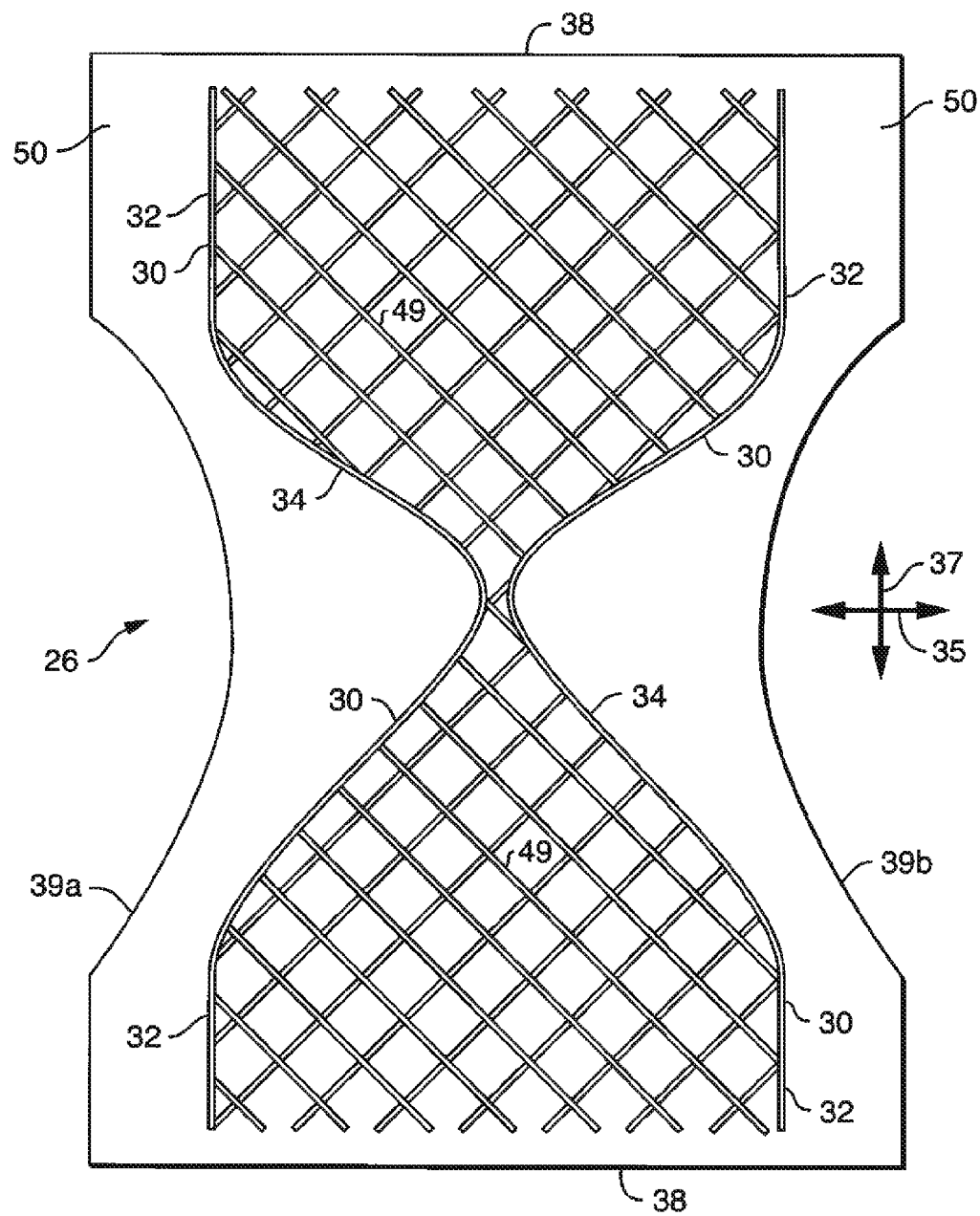
FIG. 7 representatively illustrates a plan view of another embodiment of an absorbent core incorporating principles of the present invention, shown in a laid-flat condition.
Figure 8:
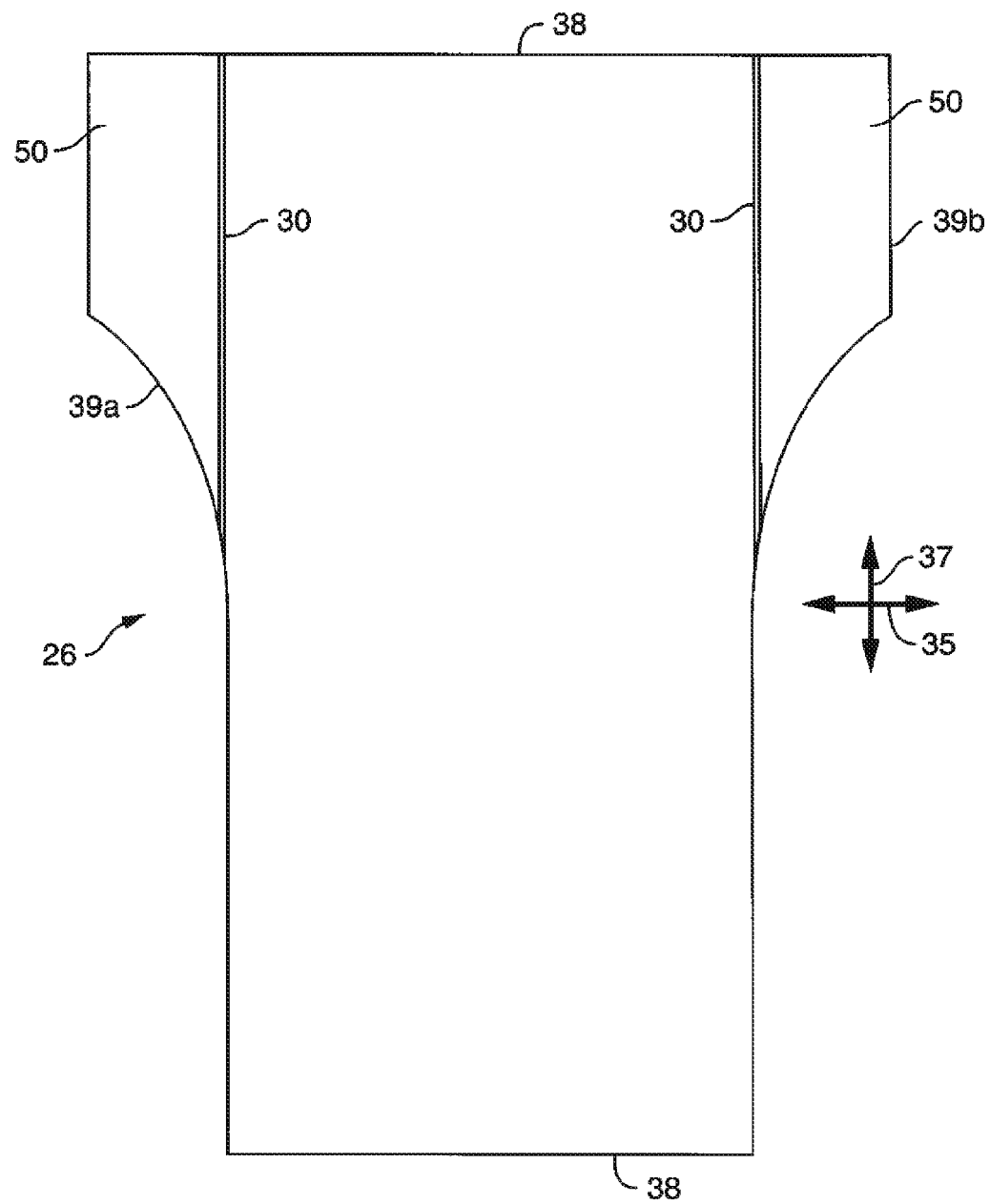
FIG. 8 representatively illustrates a plan view of another embodiment of an absorbent core incorporating principles of the present invention, shown in a laid-flat condition.

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Disposable" refers to articles which are designed to be discarded after a limited use rather than being laundered or otherwise restored for reuse.

"Emboss" and its derivatives (including "embossed" and embossing") refers to the localized application of energy to a material to increase its density. One illustrative example of embossing is the application of heat and/or pressure in a pattern of dots or line segments to a cellulosic pulp fluff pad to increase the pad's density/decrease the pad's bulk relative to un-embossed surrounding areas of the pad.

"Garment" as used herein means an article that is worn about the mid-section of the body and that covers at least a portion of the hips, lower abdomen, and lower back when worn. Examples of garments include diapers, training pants, swim trunks, incontinence underwear, enuresis underwear, briefs, other pant-like, pull-on style articles, and the like. "Garment" as used herein does not include pantyliners, menstrual pads, light incontinence pads, or other articles that are primarily intended to be worn inside of durable underpants.

"Layer" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

Reference to FIGS. 1 to 15 shall be made in describing various aspects and embodiments of the invention. It should be noted that the embodiments depicted in FIGS. 1-15 are merely representative examples of the article (or portions thereof) and the process (or portions thereof) of the invention. Although for illustrative purposes certain features of the present invention shall be described and illustrated primarily with respect to a pull-on style adult incontinence garment, the various aspects and embodiments of the present invention are also suitable for use with diapers, swim pants, training pants, enuresis garments, and the like.

In one aspect, the present invention is directed to a process 20 for manufacturing a package 22 of folded absorbent articles 24, such as folded absorbent garments. The process 20 includes providing a plurality of absorbent cores 26, such as via an interconnected web 126 of absorbent cores 26. An example of suitable absorbent core material is a liquid-absorbing mixture of pulp fluff and superabsorbent polymer, common in the industry. The core can optionally be sandwiched or encased in a liquid-permeable wrap-sheet, such as a tissue or a polyolefinic nonwoven material. The process further includes embossing at least one fold line 30 into each core 26. Each fold line 30 defines at least one fold region 32. "Fold region" as used herein refers to the portion of an embossed fold line 30 along which the absorbent core is folded. The process 20 further includes folding each core 26 along the fold region or regions 32 of each fold line 30 to create a plurality of folded absorbent articles 24. The process 20 further includes placing each folded absorbent article into a container 36.

FIGS. 1-8 representatively illustrate preferred embodiments of the cores 26 and of the embossed fold lines 30. In particular embodiments, the core is generally hourglass-shaped, as representatively illustrated in FIGS. 1-7. The absorbent cores are in particular embodiments manufactured in a longitudinal machine direction 137. Each core defines a longitudinal direction 37 and a transverse direction 35. Each core 26 defines two longitudinally opposed end edges 38, 38 and two side edges 39, 39 that extend between and interconnect the two end edges 38, 38. Each absorbent core 26 defines a longitudinal centerline 37a positioned midway between the two side edges 39, 39. As used herein, the term "edge" refers either to the line at which the component (such as a core) physically terminates (e.g., end edge 38 in FIGS. 1-8), or to the imaginary line 41 defining the boundaries of a component. For example, in FIG. 10, the imaginary lines 41 define the end edges 38, 38 of each of a plurality of interconnected absorbent cores 26.

It has been discovered that embossing fold lines 30 into absorbent cores 26 can improve the consistency and quality of packages of folded absorbent articles. Each embossed fold line 30 acts as a "guide" about which the desired fold is made during the manufacturing process. However, embossed lines in absorbent cores can impact the fluid management characteristics of absorbent articles. In particular, embossed channels can act to direct fluid along the length of the embossed channel due to increased capillary wicking, and/or can act to impede the flow of fluid in a direction normal to the length of the embossed channel in the manner of a dam. The following illustrative embodiments present a variety of approaches to managing the ability of the embossed fold lines to facilitate the desired fold as well as to managing the effect of the embossed line on the fluid-management characteristics of the core.

In particular embodiments, representatively illustrated in FIGS. 1-8, at least two fold lines 30 are embossed into each core. In other embodiments, representatively illustrated in FIGS. 1-7, at least four fold lines into each core. Each fold line can be entirely straight, as representatively illustrated in FIGS. 1-3, and 8. Alternatively, at least a portion of each fold line can be curved, as representatively illustrated in FIGS. 4-7. In particular embodiments, each fold line is continuous and unbroken, as representatively illustrated in FIGS. 1, 2, 4, 6, 7, and 8. The phrase "continuous and unbroken" means that the fold line is substantially continuous and unbroken along its entire path. In other embodiments, each fold line is discontinuous, as representatively illustrated in FIGS. 3 and 5. The term "discontinuous" means that the fold line is defined by two or more discrete segments spaced apart along the line path, but which collectively define the line path. It has been discovered that by embossing the fold line 30 as a discontinuous series of discrete line segments, fluid can more easily wick transversely past the fold line 30, such as into an ear 50 of the core 26, yet such discontinuous fold lines 30 are still effective in facilitating the folding process.

In particular embodiments, the fold region 32 of the fold line 30 extends along the entirety of the fold line 30. Examples of such embodiments are representatively illustrated in FIGS. 1-3 and 8. In other embodiments, the fold line also defines a non-fold region 34. For example, referring to FIGS. 4-7, each embossed fold line 30 defines a fold region 32 along which a fold is made in the process 20, and each embossed fold line 30 also defines a non-fold region 34 along which no fold is made in the process 20. In particular embodiments, such as those representatively illustrated in FIGS. 1-8, the fold region 32 of each fold line 30 is substantially parallel to the longitudinal centerline 37. Similarly, the fold region 32 of each fold line 30 can in particular embodiments extend in the longitudinal direction 37 proximate an ear 50.

Each fold line 30 can intersect an end edge 38 and/or a side edge 39 (FIGS. 1, 4, 5, and 8). Alternatively, each fold line 30 need not intersect either an end edge 38 or a side edge 39 (FIGS. 2, 3, 6, and 7). In particular embodiments, each fold line defines a non-fold region 34 that extends from the fold region 32 toward the longitudinal centerline 37a, representatively illustrated in FIGS. 3-7. One potential advantage of this latter configuration is that fluid that may encounter the fold line 30 during wearing of the garment will tend to be directed toward the central crotch region of the core 26, and away from the side edges 39, 39. Such non-fold regions are optional, such as the non-fold regions 34 shown in FIG. 3. Additional embossed lines may be made in the article to enhance the fluid-handling properties of the core 26 or to improve the integrity of the core 26, such as embossed line 47 in FIG. 3 or the embossed line pattern 49 in FIG. 7.

In particular embodiments, each absorbent core 26 of each article 24 with the package 22 comprises at least two transversely opposed absorbent ears 50, as is representatively illustrated in FIGS. 1-8. The term "ear" as used with respect to an absorbent core is understood in the art, and refers to a section or panel of the absorbent core that protrudes transversely further away from the longitudinal centerline 37a relative to other sections of the absorbent core along its length. Each ear 50 defines a first transverse position 52, as shown, for example, in FIGS. 11 and 14A. The process 20 includes embossing two fold lines 30 into each core 26, such that each embossed fold line 30 defines a fold region 32. In certain embodiments, such as those shown in FIGS. 1-7, each absorbent core 26 includes four absorbent ears 50—two transversely opposed front absorbent ears 50a, 50b, and two transversely opposed back absorbent ears 50c, 50d.

Referring to FIGS. 9-12, in particular embodiments, the process 20 further includes sandwiching each core 26 between a topsheet layer 60 and a backsheet layer 62 to define an absorbent assembly 70. In one approach, a topsheet web 160 and a backsheet web 170 together encase a plurality 170 of absorbent assemblies 70. Each absorbent assembly 70 has a front end 72 and a back end 74. The process 20 further includes providing a front panel web 180 that defines a front panel web waist edge 181 and a front panel web leg edge 182, and further includes providing a back panel web 184 that defines a back panel web waist edge 185 and a back panel web leg edge 186. In particular embodiments, the back panel web 184 is spaced apart from the front panel web 180. In other embodiments, instead of providing separate front and back panel webs, a single, unitary web can be provided (not shown). Desirably, the front panel web 180, the back panel web 184, or both the front and back panel webs 180/184 comprise an elastomeric material, such as a multi-layered elastomeric composite comprising two nonwoven facings sandwiching between them a series or elastomeric strands or one or more sheets of elastomeric film.

In particular embodiments, the process further includes attaching the front end 72 of each absorbent assembly 70 to the front panel web 180 and attaching the back end 74 of each absorbent assembly 70 to the back panel web 184, such as at cut-and-turn station 186. Optionally, the front panel web 180 and/or the back panel web 184 and/or the absorbent assemblies 70 can be cut to impart desired shaping to the articles 25. For example, in FIG. 9, die-cut station 188 is used to remove portions of the front and back panel webs 180, 184 and portions 89 of the absorbent assemblies 70 to provide better shape to what will later become leg openings in the articles 25. In this step on the illustrated embodiment, each absorbent assembly 70 is given an hourglass shape.

Figure 9:
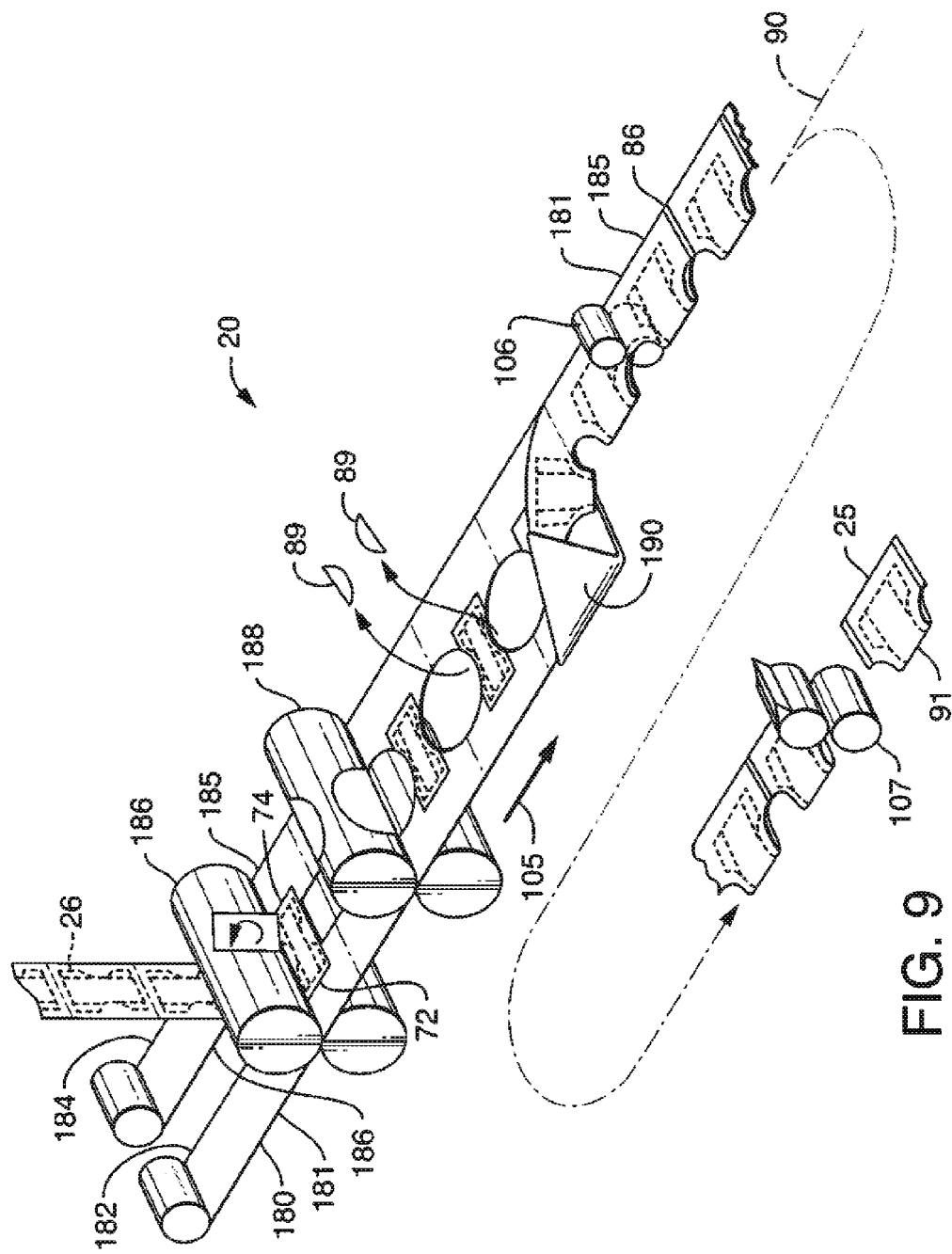
FIG. 9 representatively illustrates a perspective view of one embodiment of a manufacturing process incorporating principles of the present invention.
Figure 10A:
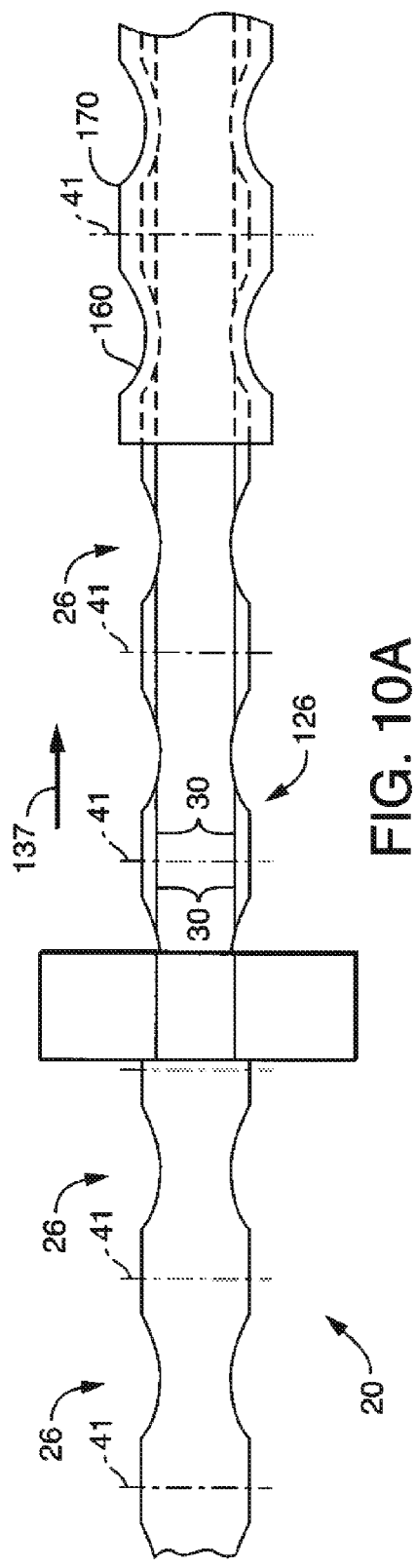
FIG. 10A representatively illustrates a plan view of one embodiment of a manufacturing process incorporating principles of the present invention.
Figure 10B:
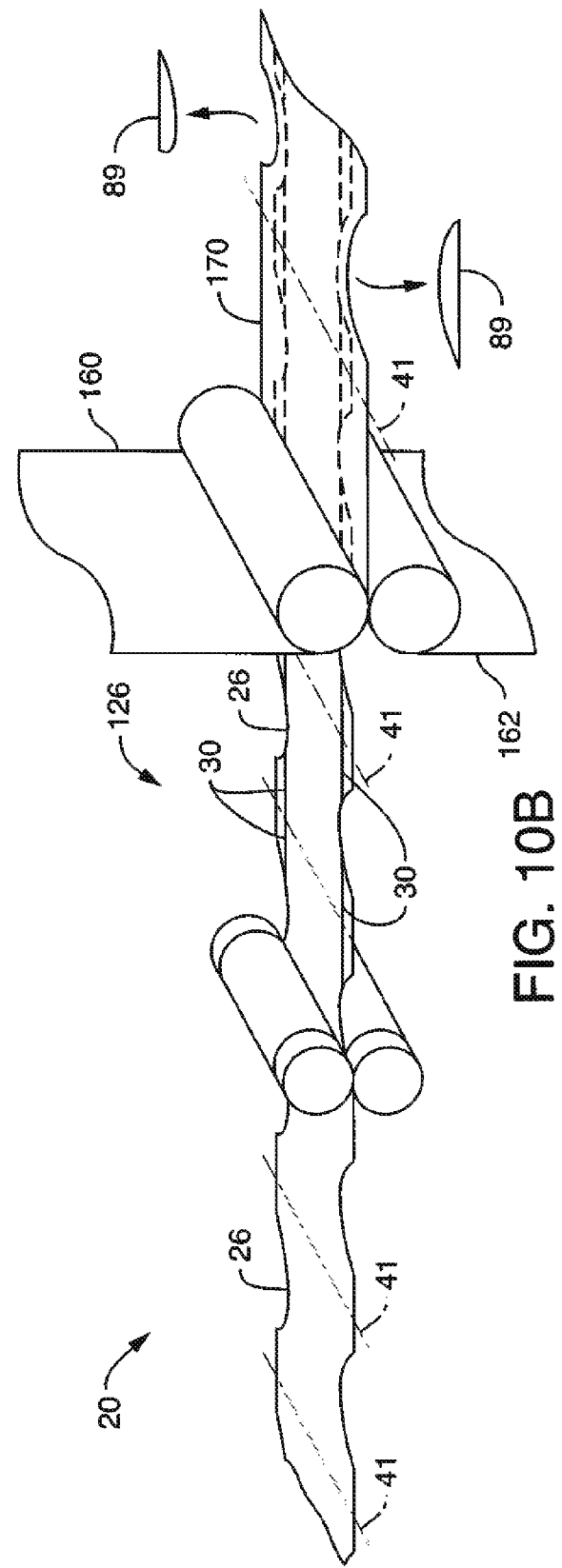
FIG. 10B representatively illustrates a perspective view of the embodiment of FIG. 10A.
Figure 11:
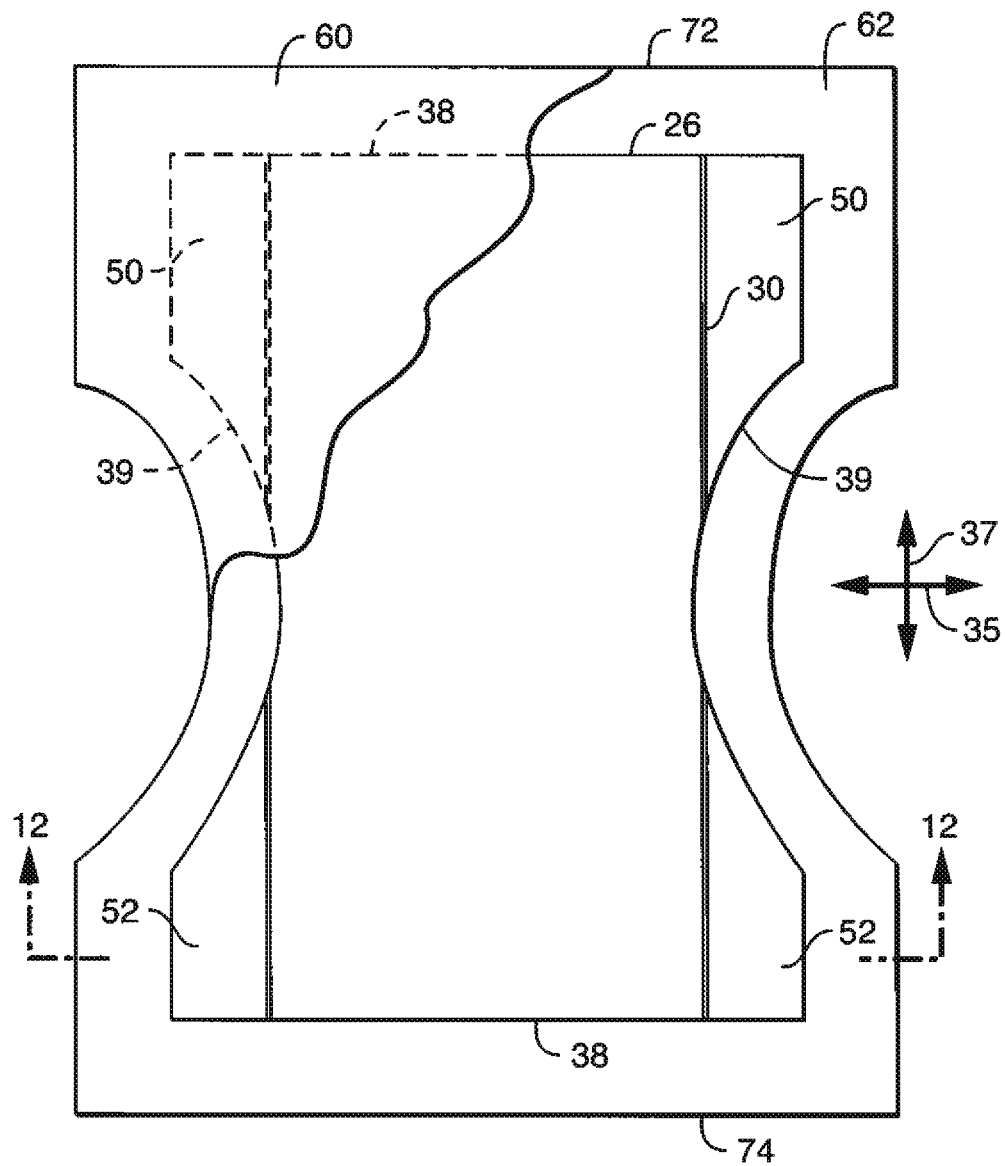
FIG. 11 representatively illustrates a plan view of an absorbent assembly incorporating principles of the present invention, with portions of the topsheet cut away to show underlying features.
Figure 12:
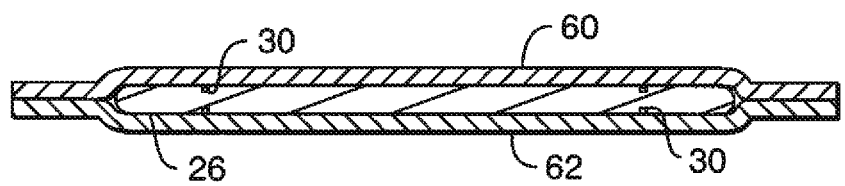
FIG. 12 representatively illustrates a cross-sectional view of the absorbent assembly of FIG. 11 taken along line 12-12 in FIG. 11.
Figure 13:
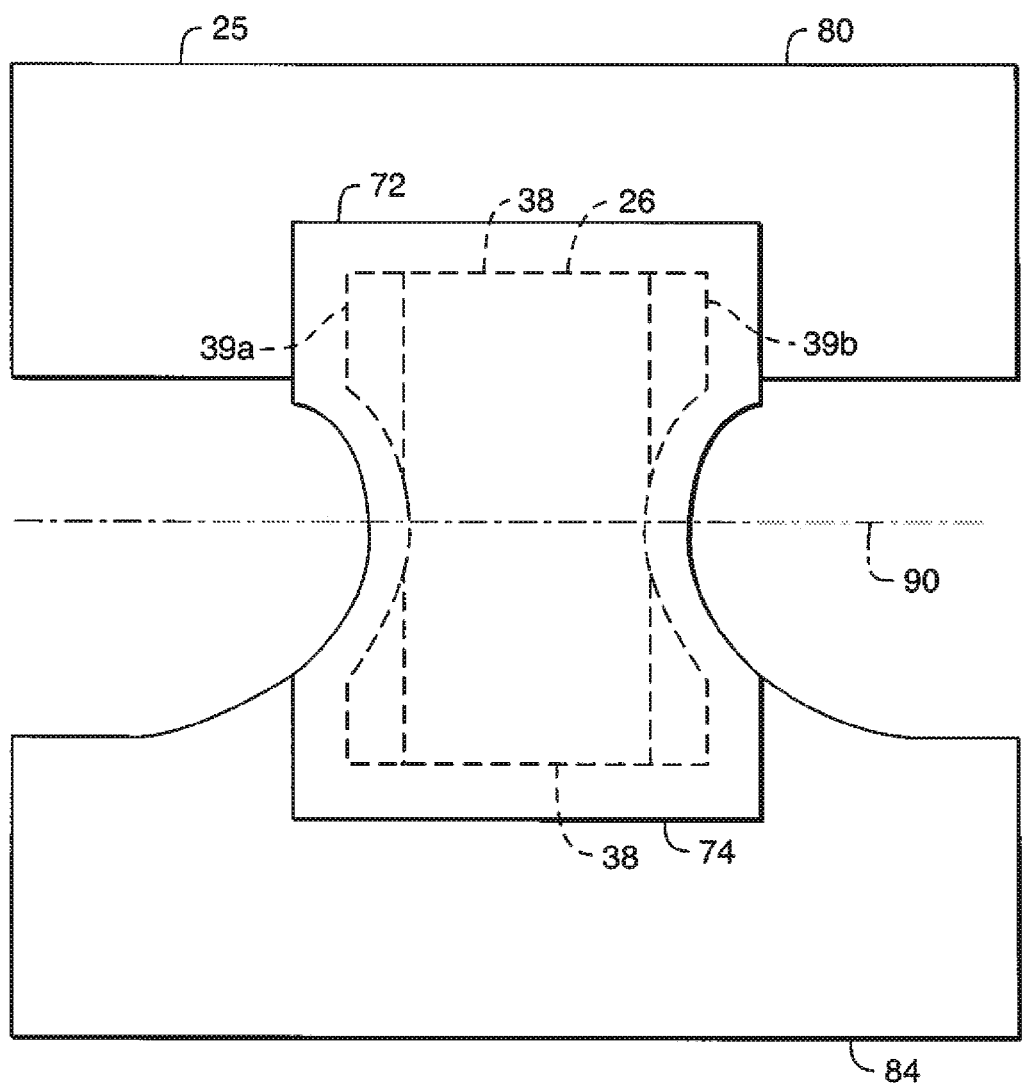
FIG. 13 representatively illustrates a front plan view of one embodiment of an absorbent garment incorporating principles of the present invention, shown in a longitudinally stretched and laid-flat condition, prior to the joining of the front and back panels, and showing the surface of the article that faces the wearer when the article is worn.

In the embodiment of FIGS. 9, 13, and 14, the process 20 further includes folding each absorbent assembly 70 along a crotch fold line 90 so as to bring the front panel web waist edge 181 into close proximity with the back panel web waist edge 185, such as at folding station 190. One or both of the front panel web waist edges 181/185 can optionally also include a separately attached or integral elastomeric waistband (not shown). Each article includes a front panel 80, a back panel 84, and an absorbent assembly 70, and each article defines a crotch fold 91. The process 20 can further include connecting each front panel 80 to each back panel 84 along a pair of side seams 86, 86 (such as at seaming station 106) to define a series of pant-like articles 25. The process 20 can further include cutting both the front panel web 180 and the back panel web 184 at a series of cuts spaced apart in a direction of web travel 105 (such as at cutting station 107) to define a series of discrete pant-like articles 25. The seams 86, 86 can be created while the front panel 80 and the back panel 84 are still an integral part of the front panel web 180 and the back panel web 184, respectively, or they can be created after the front 80 and the back panel 84 have been cut from the front and back panel webs 180, 184. Each garment 25 defines a waist opening 27 and two leg openings 29, 29.

Figure 14A:
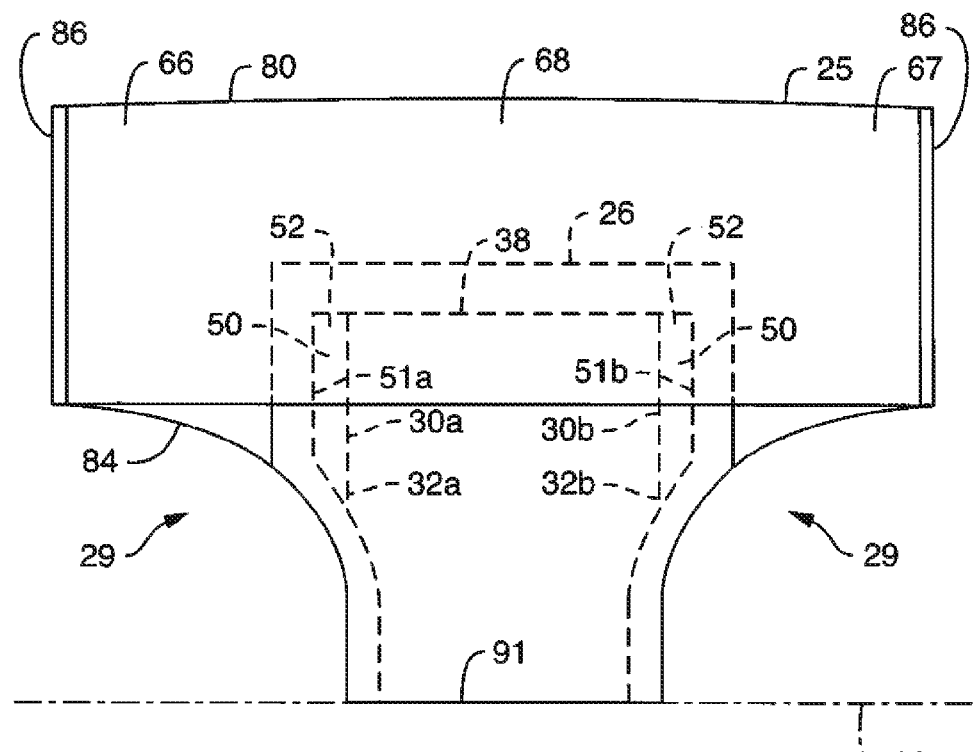
FIG. 14A representatively illustrates a front plan view of one embodiment of an absorbent garment incorporating principles of the present invention, shown in a relaxed and laid-flat condition, following the joining of the front and back panels, and showing the surface of the front of the article that faces away from the wearer when the article is worn.
Figure 14B:
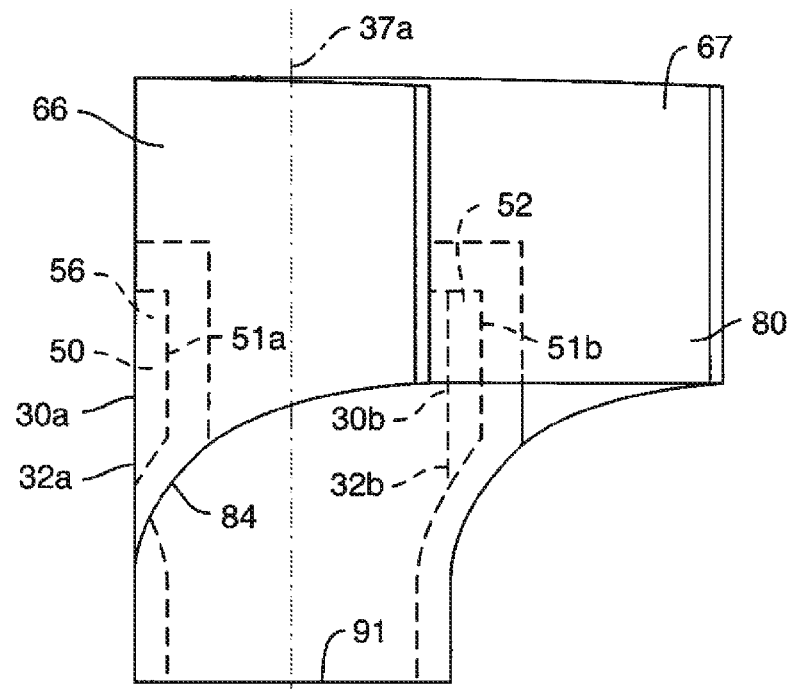
FIG. 14B representatively illustrates the garment of FIG. 14A following a fold that incorporates principles of the present invention.
Figure 14C:
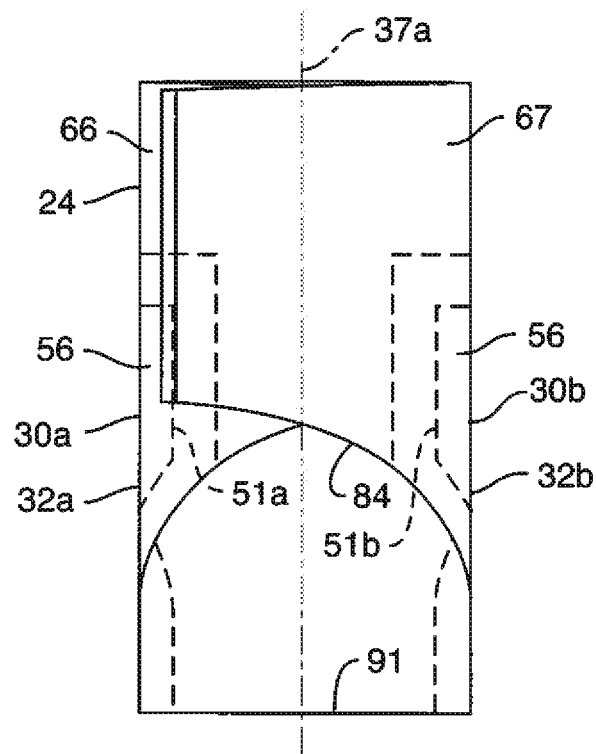
FIG. 14C representatively illustrates the garment of FIG. 14B following yet another fold that incorporates principles of the present invention.

Referring to FIGS. 14A-C, in particular embodiments, prior to folding along the fold lines 30, each ear defines a first transverse position 52. The process 20 further includes folding the core 26 of each pant-like garment 25 along the fold region 32 of each fold line 30, such that each ear assumes a second transverse position 56. The second transverse position 56 of each ear 50 is transversely inward of the first transverse position 52 of such ear 50. "Transversely inward" means in a transverse direction toward the longitudinal centerline 37a of the core 26. FIG. 14A shows the pant-like garment in a relaxed, laid-flat condition. In FIG. 14B, a first side section 66 of the garment 25 is folded over a center section 68 of the garment. In this folding step, the core 26 is folded along the fold line 30a, helping to promote a consistent, predictable fold in accordance with principles of the present invention. Similarly, in FIG. 14C, the second side section 67 of the garment 25 is folded over both the center section 68 as well as the first side section 66. Again, in this folding step, the core 26 is folded along the other fold line 30b.

Figure 14D:
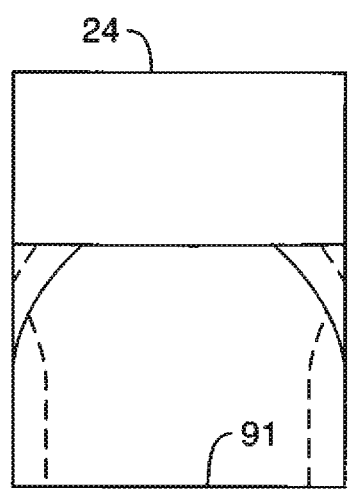
FIG. 14D representatively illustrates the garment of FIG. 14C following still another fold that incorporates principles of the present invention.
Figure 15A:
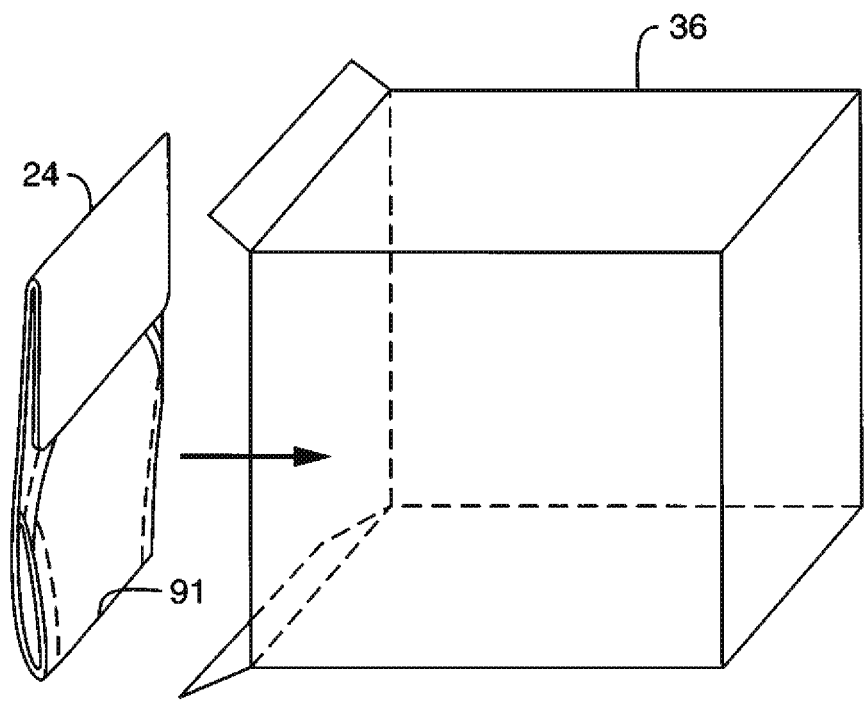
FIG. 15A representatively illustrates a perspective view of a container suitable for use in conjunction with particular embodiments of the present invention.
Figure 15B:
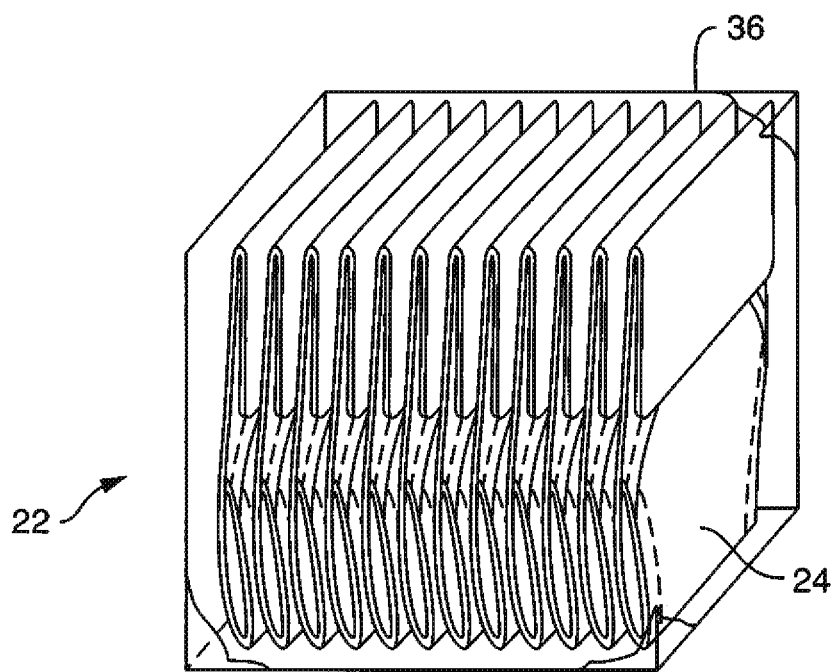
FIG. 15B representatively illustrates a perspective view of a package of folded absorbent articles incorporating principles of the present invention, with portions of the container cut away to show underlying features.

Referring to FIG. 14D, the process 20 can optionally further include folding each pant-like garment 25 so as to move the crotch fold 91 into closer proximity with the waist opening 27. A plurality of folded articles 24 is inserted into a container 36, such as a flexible bag or paperboard carton, to define the package 22 of folded disposable absorbent articles 24.

In another aspect, the present invention relates to a package 22 of folded absorbent articles 24, such as, for example, a package of folded absorbent garments made by an embodiment of the process aspect of the present invention. The package 22 includes a plurality of folded absorbent articles 24, each absorbent article comprising an absorbent core 26. Each absorbent core 26 can have any of the features of the various embodiments of the core 26 described above in conjunction with the process aspect of the invention, including but not limited to the variety of embossed fold line configurations shown and described in conjunction with FIGS. 1-8. In particular embodiments, each core defines a longitudinal direction 37 and a transverse direction 35 perpendicular to the longitudinal direction. Each core further defines two longitudinally opposed end edges 38, 38 and first and second side edges 39a, 39b that extend between and interconnect the two end edges 38, 38. Each core 26 defines a longitudinal centerline 37a positioned midway between the first and second side edges 39a, 39b.

In particular embodiments, each core comprises a first absorbent ear 50a that defines a first ear side edge 51a, and a second absorbent ear 50b that defines a second ear side edge 51b. Each core includes a first embossed fold line 30a proximate the first absorbent ear 50a and a second embossed fold line 30b proximate the second absorbent ear 50b. The first fold line 30a defines a fold region 32a and the second fold line 30b defines a fold region 32b. Each core 26 is folded along the fold region 32 of each embossed fold line 30, such that the first ear side edge 51a lies closer to the longitudinal centerline 37a than does the fold region 32a of the first embossed fold line 30a, and such that the second ear side edge 51b lies closer to the longitudinal centerline 37a than does the fold region 32b of the second embossed fold line 30b.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A process for manufacturing a package of folded absorbent garments, the process comprising:

manufacturing a plurality of absorbent cores, each core defining a longitudinal direction and a transverse direction, each core defining two longitudinally opposed end edges and two side edges that extend between and interconnect the two end edges, each absorbent core defining a longitudinal centerline positioned midway between the two side edges, each core having two transversely opposed absorbent ears, each ear defining a first transverse position;

embossing two fold lines into each core, each fold line defining a fold region;

sandwiching each core between a topsheet layer and a backsheet layer to define a plurality of absorbent assemblies, each absorbent assembly having a front end and a back end;

providing a front panel web that defines a front panel web waist edge and a front panel web leg edge;

providing a back panel web that defines a back panel web waist edge and a back panel web leg edge, the back panel web being spaced apart from the front panel web;

attaching the front end of each absorbent assembly to the front panel web and attaching the back end of each absorbent assembly to the back panel web;

folding each absorbent assembly along a crotch fold line to define a crotch fold and so as to bring the front panel web waist edge into close proximity with the back panel web waist edge;

cutting both the front panel web and the back panel web at a series of cuts spaced apart in a direction of web travel to define a series of discrete absorbent garments, each article having a front panel, a back panel, and an absorbent assembly;

connecting each front panel to each back panel along a pair of side seams to define a series of pant-like garments, each article defining a waist opening;

folding the core of each pant-like garment along the fold region of each fold line to create a plurality of folded absorbent garments, such that each ear assumes a second transverse position, the second transverse position of each ear being closer to the longitudinal centerline than the first transverse position of such ear; and placing the plurality of folded absorbent garments into a container.

2. The process of claim 1, further comprising folding each pant-like garment so as to move the crotch fold into closer proximity with the waist opening.

3. The process of claim 1, further comprising embossing at least four fold lines into each core.

4. The process of claim 1, wherein each fold line is straight, wherein each fold line intersects an end edge and a side edge, and wherein each fold region extends along the entirety of each fold line.

* * * * *